United States Patent
Palmer, III et al.

(10) Patent No.: US 9,039,688 B2
(45) Date of Patent: May 26, 2015

(54) METHOD FOR REDUCING HYPERDYNAMIC FACIAL WRINKLES

(75) Inventors: Francis R. Palmer, III, Beverly Hills, CA (US); Michael Hsu, Oakland, CA (US); Kristine Tatsutani, Redwood City, CA (US)

(73) Assignee: MyoScience, Inc., Redwood City, CA (US)

(*) Notice: Subject to any disclaimer, the term of this patent is extended or adjusted under 35 U.S.C. 154(b) by 553 days.

(21) Appl. No.: 13/325,004

(22) Filed: Dec. 13, 2011

(65) Prior Publication Data

US 2012/0265187 A1   Oct. 18, 2012

Related U.S. Application Data

(60) Provisional application No. 61/422,569, filed on Dec. 13, 2010.

(51) Int. Cl.
*A61B 18/02* (2006.01)
*A61B 18/00* (2006.01)

(52) U.S. Cl.
CPC ....... *A61B 18/02* (2013.01); *A61B 2018/00434* (2013.01); *A61B 2018/00458* (2013.01); *A61B 2018/0047* (2013.01); *A61B 2018/0293* (2013.01)

(58) Field of Classification Search
CPC ........... A61B 18/02; A61B 2018/0212; A61B 2018/00041
USPC .......................................... 606/20, 21, 22, 24
See application file for complete search history.

(56) References Cited

U.S. PATENT DOCUMENTS

| | | | | |
|---|---|---|---|---|
| 3,814,095 A | * | 6/1974 | Lubens | 604/307 |
| 5,879,378 A | * | 3/1999 | Usui | 607/96 |
| 7,250,046 B1 | * | 7/2007 | Fallat | 606/20 |
| 2004/0220497 A1 | * | 11/2004 | Findlay et al. | 600/562 |
| 2006/0224149 A1 | * | 10/2006 | Hillely | 606/21 |
| 2007/0129714 A1 | * | 6/2007 | Elkins et al. | 606/21 |
| 2008/0051776 A1 | * | 2/2008 | Bliweis et al. | 606/21 |
| 2008/0183164 A1 | | 7/2008 | Elkins et al. | |

(Continued)

FOREIGN PATENT DOCUMENTS

WO    2010/125531 A1    11/2010

OTHER PUBLICATIONS

International Search Report mailed on Apr. 6, 2012 for PCT Patent Application No. PCT/US2011/064740, 4 pages.

(Continued)

*Primary Examiner* — Christopher D Koharski
*Assistant Examiner* — Michael Carey
(74) *Attorney, Agent, or Firm* — Kilpatrick Townsend and Stockton LLP

(57) ABSTRACT

A method for cryogenically treating a target tissue comprises providing a cryogenic device having one or more tissue penetrating needle probes, and advancing the one or more tissue penetrating needle probes through skin disposed above the target tissue into the target tissue. The target tissue comprises a motor nerve. The method also includes cooling the target tissue with the one or more tissue penetrating needle probes, and temporarily disrupting signal conduction from the motor nerve thereby preventing contraction of a muscle operably coupled to the motor nerve. This reduces or eliminates hyperdynamic wrinkles of a patient's face.

42 Claims, 7 Drawing Sheets

(56) References Cited

U.S. PATENT DOCUMENTS

2008/0200910 A1  8/2008  Burger et al.
2010/0049178 A1  2/2010  Deem et al.

OTHER PUBLICATIONS

Written Opinion of the International Searching Authority mailed on Apr. 6, 2012 for PCT Patent Application No. PCT/US2011/064740, 7 pages.

Foster, K. Wade et al., "Radiofrequency Ablation of Facial Nerve Branches Controlling Glabellar Frowning," Dermatol Surg. Dec. 2009, 35(12): pp. 1908-1917.
International Preliminary Report on Patentability mailed Jun. 18, 2013, from PCT Application No. PCT/US2011/064740 (8 pages).
Extended European Search Report mailed Apr. 9, 2014, from European Application No. 11848934.3 (7 pages).

* cited by examiner

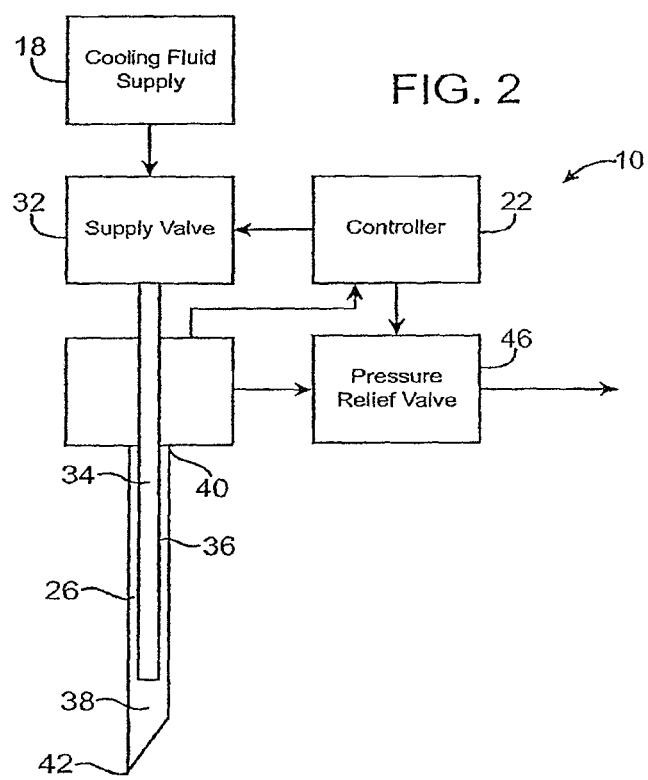

METHOD FOR REDUCING HYPERDYNAMIC FACIAL WRINKLES

CROSS-REFERENCES TO RELATED APPLICATIONS

This application claims the benefit of U.S. Provisional Application No. 61/422,569, filed on Dec. 13, 2010, the entirety of which is incorporated by reference herein.

BACKGROUND OF THE INVENTION

The present invention generally relates to medical devices, systems, and methods, particularly for reducing hyperdynamic facial wrinkles. Embodiments of the invention include devices, systems, and methods for applying cooling to dermal tissues so as to selectively remodel one or more target tissues along and/or below an exposed surface of the skin. Embodiments of the present invention may be employed for a variety of cosmetic conditions, for example, by inhibiting undesirable and/or unsightly effects on the skin such as lines, wrinkles, and cellulite dimples. Further embodiments may find use for a wide range of medical indications. For example, the remodeling of the target tissue may achieve a desired change in its behavior or composition.

The desire to reshape various features of the human body to either correct a deformity or to improve one's appearance is common. A growing number of cosmetic surgery procedures are performed annually.

Many procedures change the appearance of the skin by reducing lines and wrinkles and typically involve injecting fillers into the skin or stimulating collagen production. Pharmacologically based therapies for wrinkle alleviation and other cosmetic applications have recently gained in popularity. Botulinum toxin type A (BOTOX®) is an example of such a pharmacologically based therapy. BOTOX® is typically injected into the facial muscles to inhibit muscle contraction, resulting in temporary enervation or paralysis of the facial muscles. Once the muscle is disabled, the movement contributing to the formation of the undesirable wrinkle is temporarily eliminated. Another example of a pharmaceutical cosmetic treatment is mesotherapy, where a cocktail of homeopathic medication, vitamins, and/or drugs approved for other indications is injected into the skin to deliver healing or corrective treatment. Various cocktails are intended to effect body sculpting and cellulite reduction by dissolving adipose tissue or resurface skin via collagen enhancement.

There are also non-pharmacologically based cosmetic treatments. For example, endermology is a mechanical therapy utilizing vacuum suction to stretch or loosen fibrous connective tissues which may cause the dimpled appearance of cellulite.

While BOTOX® and mesotherapies may temporarily reduce lines and wrinkles, reduce fat, or provide other cosmetic benefits, they are not without their drawbacks. Particularly, there are dangers associated with the injection of a known toxic substance or an unknown or untested cocktail into a patient. Additionally, while the effects of endermology are not known to be potentially dangerous, they are brief and only mildly effective.

In light of the above, it would be desirable to provide medical devices and methods that provide a non-toxic, minimally invasive treatment for tissue with minor or no side effects. Medical devices, systems, and methods utilizing a cryogenic approach to treating tissue, particularly for cosmetic defects such as wrinkles, excess fat, and cellulite, have been proposed. These medical devices, systems, and methods may be used in lieu of or compliment known pharmacologically or non-pharmacologically based cosmetic therapies. Ideally, they should allow the injection of toxins and harmful cocktails to be minimized or avoided while providing similar or improved cosmetic results. Recovery time from therapy, i.e., patient "down-time," may also be reduced because these procedures may be performed percutaneously, with only local or no anesthetic, with minimal or no cutting of the skin, no need for suturing or other closure methods, no extensive bandaging, and limited or no bruising or other factors contributing to extended patient recovery. Additionally, cryogenic treatments are also desirable since they may be used in the treatment of other cosmetic and/or dermatological conditions (and potentially for other target tissues), particularly where the treatments may be provided with greater accuracy and control, less collateral tissue injury and/or pain, and greater ease of use.

Some examples of cryotherapy systems include those described in U.S. Pat. Nos. 5,647,868, 6,277,116, 6,858,025, and 7,083,612 as well as U.S. Patent Application Publication No. 2004/0215294 A1 (patented).

More references that may be of interest include U.S. Pat. Nos. 5,334,181, 6,032,675, 6,706,037 and 5,334,181 and "A model for the time dependent three-dimensional thermal distribution within iceballs surrounding multiple cryoprobes": Rewcastle et al; Medical Physics, Vol. 28, No. 6, June 2001; and "Laboratory Evaluation of Ice Formation around a 3-mm Accuprobe": Saliken et al; Cryobiology 32, 285-295 (1995).

Various devices for treatment of motor nerves are currently being developed. For example, some devices treat motor nerves of the face using heat applied by a radiofrequency probe (RF). The treatment also involves the use of electrical stimulation to identify specific treatment locations, followed by a treatment at the identified location with RF energy. While this procedure appears promising, in certain situations, the procedure may be challenging to perform. It may be painful, may require patient sedation, may be time consuming, and may have side effects. Furthermore, it has been shown that heat applied to nerves may lead to spurious regrowth and neuroma formation. Therefore, using cryotherapy through microneedles inserted using anatomical landmarks for targeting the treatment area may provide a more clinically viable procedure with local anesthetic and no permanent damage to nerves and benign side effects.

Therefore, given the challenges of current technology, a need exists for improved devices, systems, and methods, particularly for treating wrinkles of the face. At least some of these objectives will be met by the present invention.

BRIEF SUMMARY OF THE INVENTION

The present invention relates to medical devices, systems, and methods. More particularly, the present invention relates to the treatment of hyperdynamic wrinkles of tissue, especially in the face.

One embodiment of the invention relates to a method for cryogenically treating a target tissue. In the method, a cryogenic device having one or more tissue penetrating needle probes can be provided. The one or more tissue penetrating needle probes can be advanced through skin disposed above the target tissue into the target tissue. The target tissue can include a motor nerve. The method also may include cooling the target tissue with the one or more tissue penetrating needle probes, and temporarily disrupting signal conduction from the motor nerve thereby preventing contraction of a muscle operably coupled to the motor nerve. This can reduces or eliminate hyperdynamic wrinkles of a patient's face.

In one aspect, the one or more tissue penetrating needle probe may comprise a multi-needle array.

In another aspect, anatomical landmarks may be identified prior to advancing the one or more tissue penetrating needle through the skin.

In another aspect, anatomical landmarks may be identified by palpation, or by applying electrical stimulation, imaging, or locally injecting a substance.

In another aspect, a template may also be applied to the patient's face to facilitate identification of the anatomical landmarks.

In another aspect, the one or more tissue penetrating needle probes may be inserted substantially perpendicular to the target tissue, or they may be inserted substantially parallel to the target tissue.

In another aspect, the target tissue may comprise the angular nerve, and the one or more tissue penetrating needle probes may be inserted adjacent the frontomaxillary suture or the frontonasal suture.

In another aspect, the target tissue may comprise the angular nerve, and the one or more tissue penetrating needle probes may be inserted inferior or medial to the infraorbital foramen.

In another aspect, the cooling step may include cooling the target tissue starting adjacent a lateral edge of an orbital rim on the patient's face, and the cooling may extend posteriorly toward a hairline of the patient's face.

In another aspect, the cooling step may also include cooling the target tissue starting adjacent the tragus, and the cooling may progress anteriorly along the zygomatic arch of the patient's face.

In another aspect, the disruption may include Wallerian degeneration of the motor nerve.

In another aspect, temporal branch of the motor nerve adjacent an orbital rim may be temporarily disrupted.

In another aspect, the method may further include protecting the skin disposed above the target tissue from cooling induced injury.

In another aspect, protecting the skin may include heating the skin disposed above the target tissue.

In another aspect, a portion of the patient's face may also be locally anesthetized before, during, or after the treatment.

Another embodiment of the invention relates to yet another method for cryogenically treating a target tissue. In the method, a cryogenic device having one or more tissue penetrating needle probes can be provided. Further, a treatment template having alignment feature and a treatment guideline can also be provided. The treatment template can be aligned on a temple region of a patient using the alignment feature. The treatment template can be maintained on the template region or a treatment path can be marked along the treatment guideline. Along the treatment guideline or marked treatment path the one or more tissue penetrating needle probes can be advanced through skin disposed above the target tissue into the target tissue. The target tissue can include a motor nerve. The target tissue can be cooled with the one or more tissue penetrating needle probes. Signal conduction from the motor nerve can be temporarily disrupting thereby preventing contraction of a muscle operably coupled to the motor nerve, and thus reduce or eliminate hyperdynamic wrinkles of a patient's face.

In one aspect, the alignment feature includes a first corner, and a bottom edge leads from the first corner, and a side edge leads from the first corner to a second corner.

In another aspect, aligning the treatment template includes placing the first corner at a lateral canthus on the temple region.

In another aspect, aligning the treatment template further includes aligning the bottom edge in an anterior to posterior direction.

In another aspect, the treatment guideline can extend from the second corner at an angle of approximately 30 degrees.

In another aspect, the treatment template can be a flexible plastic sheet.

In another aspect, the treatment template may be constructed from adhesive tape.

In another aspect, the adhesive tape can include a medication.

In another aspect, the adhesive tape can include a heating element.

In another aspect, the skin may be heated during cooling using the heating element.

Another embodiment of the invention relates to a template for cryogenically treating a target tissue. The template can include a planar body having an alignment feature for aligning the planar body with a lateral canthus on a temple region of a face, the temple region having target tissue. A treatment guide feature can be proximate to the first corner. The treatment guide feature can be configured to guide one or more tissue penetrating needle probes through skin disposed above the target tissue into the target tissue, the target tissue comprising a motor nerve.

In one aspect, the alignment feature of the template includes a first corner, with a bottom edge leading from the first corner. A side edge can lead from the first corner to a second corner.

In another aspect, the treatment guideline of the template can extend from the second corner at an angle of approximately 30 degrees.

In another aspect, the planar body can be a flexible plastic sheet.

In another aspect, the planar body can be adhesive tape.

In another aspect, the adhesive tape includes a topical anesthesia medication.

In another aspect, the adhesive tape includes a heating element.

These and other embodiments are described in further detail in the following description related to the appended drawing figures.

BRIEF DESCRIPTION OF THE DRAWINGS

FIG. 2 schematically illustrates components that may be included in the treatment system, according to an embodiment of the invention.

DETAILED DESCRIPTION OF THE INVENTION

Figure 1A:
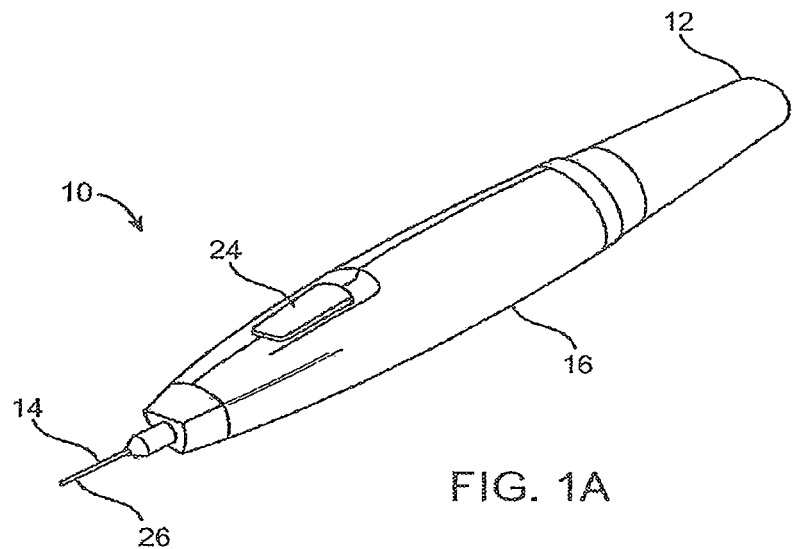
FIG. 1A is a perspective view of a self-contained subdermal cryogenic remodeling probe and system, according to an embodiment of the invention.

The present invention provides improved medical devices, systems, and methods. Embodiments of the invention will facilitate remodeling of tissues disposed at and below the skin, optionally to treat a cosmetic defect, a lesion, a disease state, and/or so as to alter a shape of the overlying skin surface.

Embodiments of the present invention also provide an array of multiple probes that enables both the treatment of a larger volume of tissue and enables the treatment to be performed at a uniform targeted temperature. The use of multiple probes arranged in various configurations around a target treatment zone creates a consistent, predictable and uniform isothermal region in tissue.

Additional control of the treatment zone can be controlled by indexing the distal end of the probe against an insulative surface such as bone, and at the proximal end of the treatment zone by applying heat to the surface tissue.

Among the most immediate applications of the present invention may be the amelioration of lines and wrinkles, particularly by inhibiting muscular contractions which are associated with these cosmetic defects. Rather than relying entirely on a pharmacological toxin or other bioactive agent to disable muscles so as to induce temporary paralysis, many embodiments of the invention will at least in part employ cold to immobilize muscles. Advantageously, nerves, muscles, and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −90° C. In some embodiments, apoptosis may be induced using treatment temperatures from about −1° C. to about −15° C., or from about −1° C. to about −19° C. Colder temperatures down to −90° C. may also be used. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling for treatment of cosmetic and other defects may be found in U.S. Patent Publication No. 2007/0129717 (patented), filed on Dec. 5, 2005 and entitled "Subdermal Cryogenic Remodeling of Muscle, Nerves, Connective Tissue, and/or Adipose Tissue (Fat)," and U.S. Patent Publication No. 2008/0183164 (patented), filed on Jun. 28, 2007 also entitled "Subdermal Cryogenic Remodeling of Muscles, Nerves, Connective Tissue, and/or Adipose Tissue (Fat)," the full disclosures of which are both incorporated herein by reference.

In addition to cosmetic treatments of lines, wrinkles, and the like, embodiments of the invention may also find applications for treatments of subdermal adipose tissues, benign, pre-malignant lesions, malignant lesions, acne and a wide range of other dermatological conditions (including dermatological conditions for which cryogenic treatments have been proposed and additional dermatological conditions), and the like. Embodiments of the invention may also find applications for alleviation of pain, including those associated with muscle spasms as disclosed in copending U.S. Patent Publication No. 2009/0248001 (patented), the full disclosure of which is incorporated herein by reference.

Figure 1B:
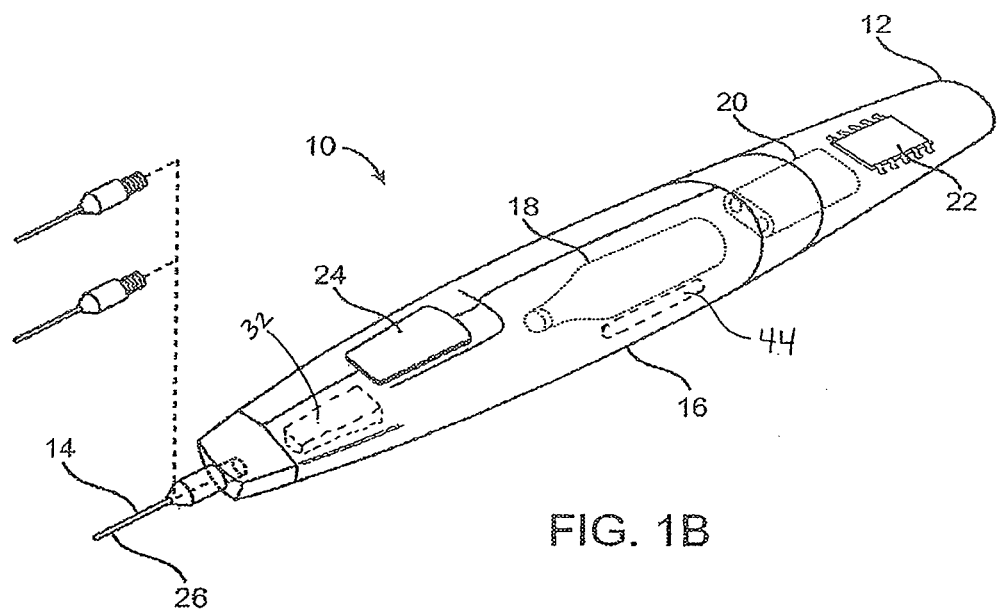
FIG. 1B is a partially transparent perspective view of the self-contained probe of FIG. 1A, showing internal components of the cryogenic remodeling system and schematically illustrating replacement treatment needles for use with the disposable probe.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen in FIG. 1B, a cryogenic cooling fluid supply 18, a supply valve 32 and electrical power source 20 are found within housing 16, along with a circuit 22 having a processor for controlling cooling applied by self-contained system 10 in response to actuation of an input 24. Power source 20 also supplies power to heater element 44 in order to heat the cooling fluid supply 18 thereby helping to create uniform coolant conditions. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may be absent.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 27 g needle having a sharpened distal end that is axially sealed. Probe 26 may have an axial length between distal end 14 of housing 16 and the distal end of the needle of between about 0.2 mm and 5 cm, preferably having a length from about 0.3 cm to about 0.6 cm. Such needles may comprise a stainless steel tube with an inner diameter of about 0.007 inches and an outer diameter of about 0.016 inches, while alternative probes may comprise structures having outer diameters (or other lateral cross-sectional dimensions) from about 0.006 inches to about 0.100 inches. Generally, needle probe 26 will comprise a 16 g or smaller size needle, often comprising a 20 g needle or smaller, typically comprising a 25 g or smaller needle. In some embodiments, probe 26 may comprise two or more needles arranged in a linear array, such as those disclosed in U.S. Patent Publication No. 2008/0183164 (patented), filed on Jun. 28, 2007 and entitled "Subdermal Cryogenic Remodeling of Muscles, Nerves, Connective Tissue, and/or Adipose Tissue (Fat)," the full disclosure of which has been incorporated herein by reference. Multiple needle probe configurations allow the cryogenic treatment to be applied to a larger or more specific treatment area. Other needle configurations that facilitate controlling the depth of needle penetration and insulated needle embodiments are disclosed in U.S. Patent Publication No. 2008/0200910 (patented), filed Feb. 16, 2007 and entitled "Replaceable and/or Easily Removable Needle Systems for Dermal and Transdermal Cryogenic Remodeling," the entire contents of which are incorporated herein by reference. In some embodiments, needle 26 is releasably coupled with body 16 so that it may be replaced after use with a sharper needle (as indicated by the dotted line) or with a needle having a different configuration. In exemplary embodiments, the needle may be threaded into the body, it may be press fit into an aperture in the body or it may have an optional quick disconnect such as a detent mechanism for engaging the needle with the body. The optional quick disconnect may also have a check valve which can be advantageous since it permits decoupling of the needle from the body at any time without excessive coolant discharge. This can be a useful safety feature in the event that the device fails in operation (e.g. motor failure), allowing an operator to disengage the needle and device from a patient's tissue without exposing the patient to coolant as the system depressurizes. This feature is also advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 comprises a canister, sometimes referred to herein as a cartridge, containing a liquid under pressure, with the liquid preferably having a boiling temperature of less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit the temperature, time, rate of temperature change, or other cooling characteristics. The valve will often be powered electrically via power source 20, per the direction of processor 22, but may at least in part be manually powered. The exemplary power source 20 comprises a rechargeable or single-use battery. The power source may also be provided by an A/C power supply, such as a wall socket coupled to the facility mains. Additional details about valve 32 and power source 20 are described below.

The exemplary cooling fluid supply 18 comprises a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2O$ canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Referring now to FIG. 2, the flow of cryogenic cooling fluid from fluid supply 18 is controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in U.S. Patent Publication No. 2008/0200910 (patented), previously incorporated herein by reference.

Still referring to FIG. 2, a heater (not illustrated) heats cooling fluid supply 18 so that heated cooling fluid flows through valve 32 and through a lumen 34 of a cooling fluid supply tube 36. Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 μm, the inner diameter often being less than about 100 μm, and typically being less than about 40 μm. Exemplary embodiments of supply tube 36 have inner lumens of between about 15 and 50 μm, such as about 30 μm. An outer diameter or size of supply tube 36 will typically be less than about 1000 μm, often being less than about 800 μm, with exemplary embodiments being between about 60 and 150 μm, such as about 90 μm or 105 μm. The tolerance of the inner lumen diameter of supply tubing 36 will preferably be relatively tight, typically being about +/−10 μm or tighter, often being +/−5 μm or tighter, and ideally being +/−3 μm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Patent Publication No. 2008/0154254 (pending), filed Dec. 21, 2006 and entitled "Dermal and Transdermal Cryogenic Microprobe Systems and Methods," the entire contents of which are incorporated herein by reference. U.S. Patent Publication No. 2008/0200910 (patented), previously incorporated herein by reference, also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the energy required to vaporize the cooling fluid and/or heat the gas, cools the tissue engaged by the needle. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 (expired) previously incorporated herein by reference. Thus, the relief valve allows better temperature control in the needle, minimizing transient temperatures. Further details on exhaust volume are disclosed in U.S. Patent Publication No. 2008/0200910 (patented), previously incorporated herein by reference.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in U.S. Patent Publication No. 2008/0154,254 (pending), previously incorporated herein by reference.

Figure 3:
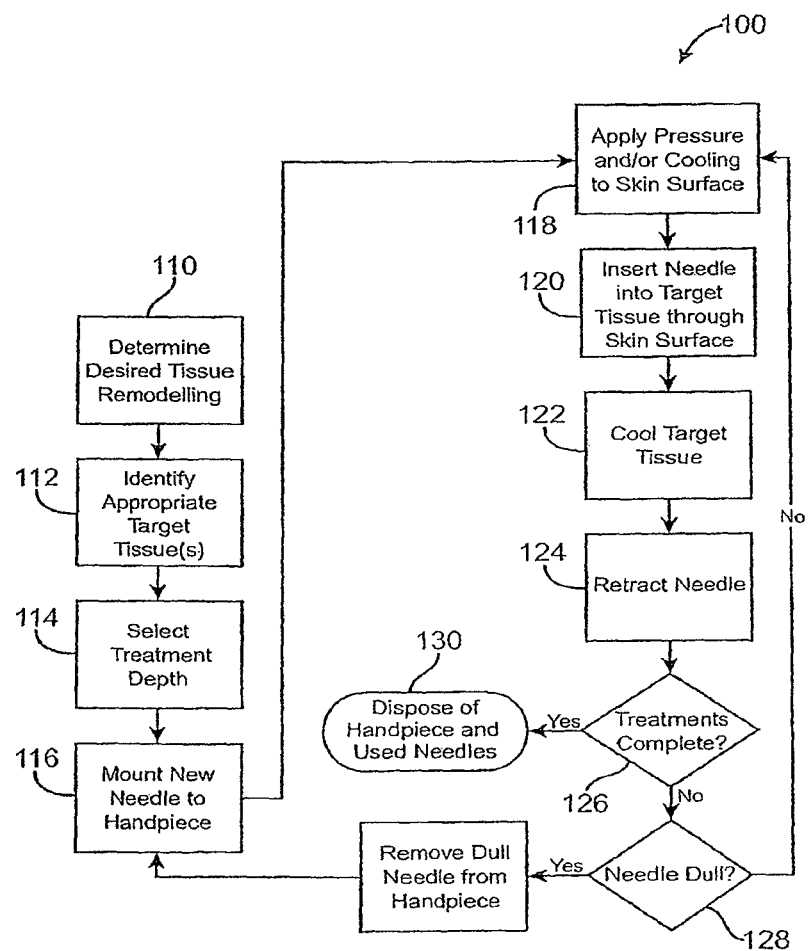
FIG. 3 is a flow chart schematically illustrating a method for treatment using the disposable cryogenic probe and system of FIG. 1B.

Referring now to FIG. 3, a method 100 facilitates treating a patient using a cryogenic cooling system having a self-contained reuseable handpiece, replaceable needles such as those of FIG. 1B and a limited capacity battery, or powered by an A/C supply. In some embodiments, the handpiece may also be a single patient disposable device. Method 100 generally begins with a determination 110 of the desired tissue remodeling and results, such as the alleviation of specific cosmetic wrinkles of the face, the inhibition of pain from a particular site, the alleviation of unsightly skin lesions or cosmetic defects from a region of the face, or the like. Appropriate target tissues for treatment are identified 112 (such as the subdermal muscles that induce the wrinkles, a tissue that transmits the pain signal, or the lesion-inducing infected tissues), allowing a target treatment depth, target treatment temperature profile, or the like to be determined 114. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Figure 4:
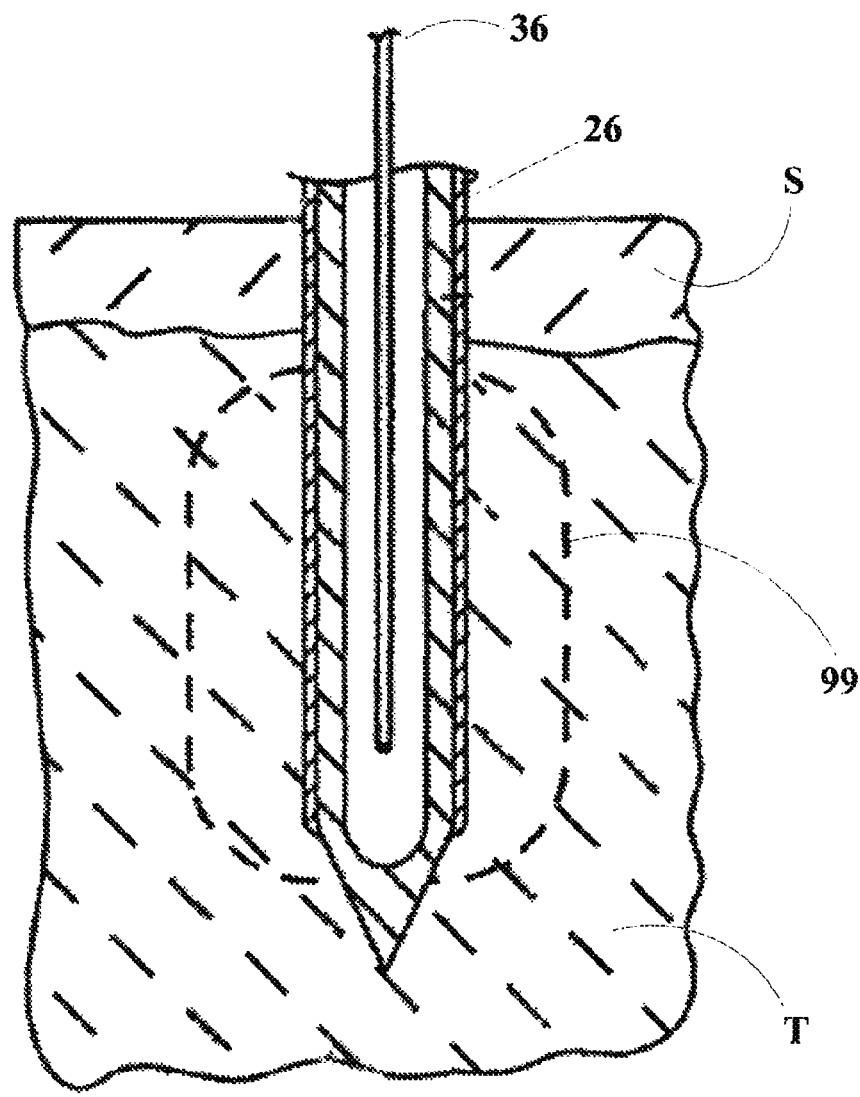
FIG. 4 illustrates the cryogenic probe of FIG. 1B inserted through a patient's skin into target tissue, according to an embodiment of the invention.

Pressure, cooling, or both may be applied 118 to the skin surface adjacent the needle insertion site before, during, and/or after insertion 120 and cryogenic cooling 122 of the needle and associated target tissue. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used handpiece and needles can be disposed of 130. In some cases, the power source used to provide energy to the system is a battery and this may be replaced or re-charged when depleted. FIG. 4 illustrates the needle 26 of FIGS. 1A-1B and FIG. 2 after it has pierced through a patient's skin S and into the adjacent treatment tissue T. After cryogenic cooling fluid is heated and in injected into the needle 26 via supply tube 36, a region 99 of target tissue T is cooled sufficiently to effect the desired remodeling of at least a portion of the target tissue.

A variety of target treatment temperatures, times, and cycles may be applied to differing target tissues so as to achieve the desired remodeling. For example, (as more fully described in U.S. Patent Publication Nos. 2007/0129714 (patented) and 2008/0183164 (patented), both previously incorporated herein by reference) desired temperatures may be used that temporarily and/or permanently disable or interfere with muscle or nerve contractile function. Also temperatures may be used that protect the skin and surrounding tissues.

There is a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of apoptosis and necrosis may also provide long-lasting or permanent benefits. For the reduction of adipose tissue, a permanent effect may be advantageous. Surprisingly, both apoptosis and necrosis may produce long-term or even permanent results in adipose tissues, since fat cells regenerate differently than muscle cells.

In preferred embodiments, the exemplary cryogenic devices may be used to treat hyperdynamic wrinkles of the face. Such hyperdynamic wrinkles of the skin are associated with contraction of a muscle, for example, when the eyebrows are lifted, wrinkles form on the forehead. Therefore, the ability of motor nerves to conduct signals to the target facial or other muscle(s) may be disrupted, ideally, through exposure of the nerve to a controlled low temperature environment. The disruption of the signal path prevents the muscles that generate hyperdynamic facial wrinkles from activating, and therefore eliminates hyperdynamic facial wrinkles. The disruption is preferably temporary and the normal function returns within weeks or months. The type of nerve injury caused by low temperatures has been described in the literature as Wallerian Degeneration.

In an exemplary method, the temporal branch of the facial nerve which feeds the frontalis, corrugator supercilii, and other facial muscles, the angular nerve, which enervates the corrugator supercilii and the procerus muscle, or nerves that enervate other facial muscles can be temporarily disrupted by applying cold therapy in anatomically based patterns in the temporal and other regions of the face. The disruption can be performed by using a cryoprobe that decreases the local environmental temperature sufficiently cold to induce a nerve block. The cryoprobe can be designed and constructed so as to minimize local collateral tissue trauma during the treatment by using short exposure times to cold, using small gauge needles, and by providing protection of the dermis by dermal warming, provided as an integral part of the cryoprobe or separately. The procedure can be designed to minimize patient discomfort through use of local anesthetics. Also the procedure can be performed simply with minimal discomfort and a short procedure time by targeting the treatment location with appropriate anatomical landmarks and designing the cryoprobe and cryotherapy to provide optimum treatment in minimum time.

In preferred embodiments, the hyperdynamic wrinkles associated with raising the eyebrows can be eliminated by using a cryoprobe such as those previously described above to treat the facial nerve in the temporal region (side of the head near the orbital rim) by first palpating the area, identifying anatomical landmarks, measuring or applying a predetermined template to/from or between the identified landmarks, and inserting a cryoprobe in a pattern that causes a sufficient number of local facial nerve branches in the target area to be impacted by the cold treatment.

The method preferably comprises disruption the conduction a motor nerve in order to minimize the appearance of hyperdynamic facial wrinkles in the forehead, frown, crow's feet and other areas of the face. This disruption may be achieved through a mechanical means such as cutting the nerve or crushing or compressing it. Alternatively the disruption may be achieved through pharmaceutical means or through the application of energy (radio frequency, high intensity ultrasound, etc.), or preferably through the application of cold to trigger axonotmesis in the motor nerve. Alternatively multiple modalities may be used together.

One preferred treatment of hyperdynamic wrinkles involves the disruption of conduction of the motor nerve in the temporal region of the face. Preferably, the treatment pattern will start at or near the lateral edge of the orbital rim and extend posteriorly toward the hairline, ending when the desired treatment effect is observed in the patient or at the hair line. Or, alternatively the treatment pattern will start near the tragus and progress anteriorly along the zygomatic arch until the desired effect is achieved.

Figure 5:
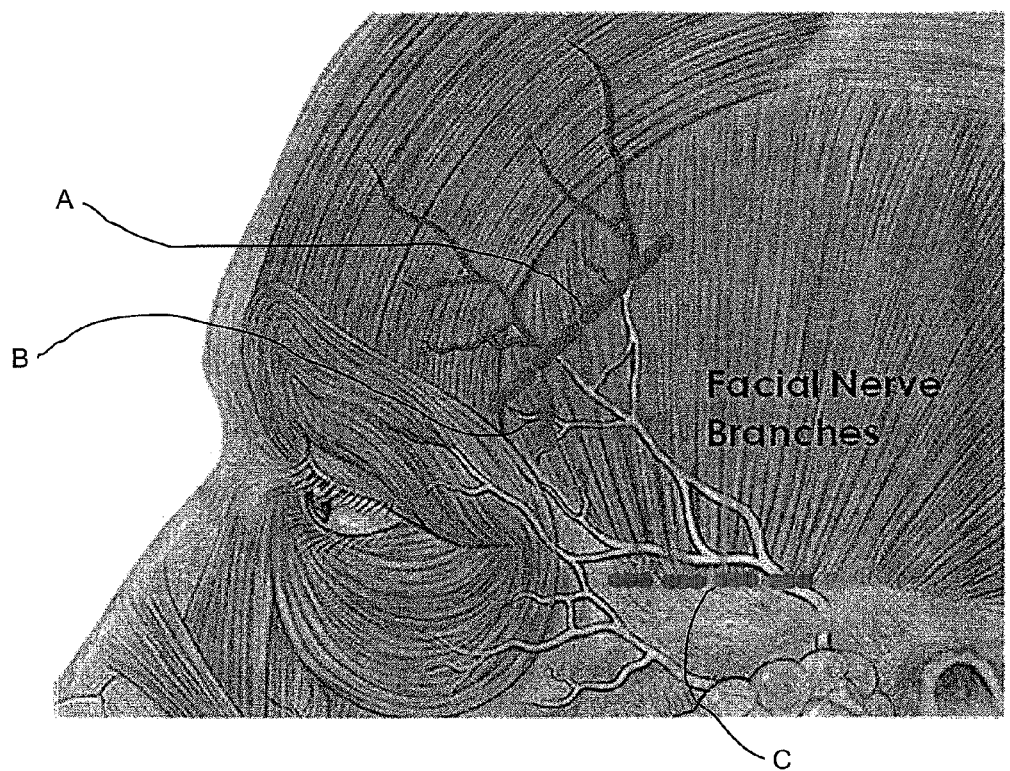
FIG. 5 illustrates treatment paths along some of the facial nerve branches along the face, according to an embodiment of the invention.

The treatment of horizontal forehead wrinkles may preferably be performed by first palpating the outer edge of the lateral orbital rim and the temporal ridge. The cryogenic needle probe array is then inserted into the tissue. This cryogenic needle array is preferably a two or three needle linear array, but other numbers of needles and geometries of the array can be used from 1 to 6 needles. In some number of treatments, the needle array would be placed adjacent to the lateral edge of the orbital rim, at or near the intersection of the orbital rim and the temporal ridge. The cryogenic needle probe array is then aligned either perpendicular to, or parallel to the orbital rim, or at some angle to the rim. In subsequent treatments the cryogenic needle probe array is placed posterior to the lateral orbital rim, proceeding in a linear manner towards the hairline. Treatments may be stopped after the desired effect has been achieved, or treatment may be continued to or even past the hairline. The angle of the needles relative to the skin surface can be parallel, perpendicular, or at any angle relative to the surface. Additional treatments could be performed at the same location, or near to the location of a previous treatment. Three examples of diagonal, vertical, and horizontal treatment patterns, respectively A, B, and C, are illustrated in FIG. 5. The treatment would be performed using a probe that could provide a treatment along the entire length of the needles, or could provide a treatment preferential to a particular location where the nerve resides. The system could also protect structures, such as the dermis and epidermis, during the cryogenic treatment. If the desired effect was produced, the procedure could be finished, or alternatively additional treatments could be performed.

In order to treat the angular nerve, a cryogenic needle probe array would be inserted near the frontomaxillary suture and/or the frontonasal suture. Or, alternatively the angular nerve treatment could be performed inferior and/or medial to the infraorbital foramen.

Alternatively treatments for other areas of the face could be performed at any other location along these or other motor nerves by insertion of needle probe arrays of appropriate number and geometry for the target anatomy. Treatments could also be performed at multiple locations along different branches of the same nerve or different nerves.

Means of locating the nerve can be physical palpation using anatomical landmarks or other modalities such as electrical stimulation, imaging modalities, and local injections of anesthetics. Or, any combination of modalities could be used. The modalities could be incorporated into the device or be separate.

Preferably, the treatment will be performed with 25 g or smaller needles, more preferably from 27 g to 30 g or smaller. A single needle or multiple needle linear or other geometries in order to be appropriate for the anatomical area being treated and to maximize the treatment region per probe insertion. Ideally, the treatment will create a region of sufficiently coldness to cause the nerves in that region to stop conducting, thus induce a nerve block.

Preferably, the treatment will be performed incorporating protection of the skin from excessive heat or cold. Ideally the treatment will be performed with the needle(s) introduced perpendicular to the skin surface, but alternatively the needle (s) could be introduced in parallel to the skin surface or at any angle relative to the surface. The system for performing the treatments would ideally be a handheld cryogenic refrigeration system using an array of microrefrigeration needles such as those described above, as well as in described in US Patent Publication No. 2008/0183164 (patented), the entire contents of which are incorporated herein by reference. Exemplary embodiments of skin protection methods including heater elements are disclosed in International PCT Patent Publication No. WO2010/075448 (expired), the entire contents of which are incorporated herein by reference.

Figure 6B:
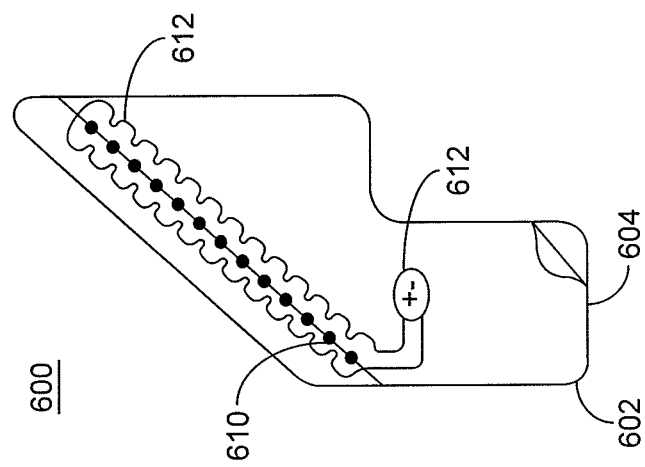
FIGS. 6A and 6B are top views of treatment templates, according to embodiments of the invention.
Figure 6A:
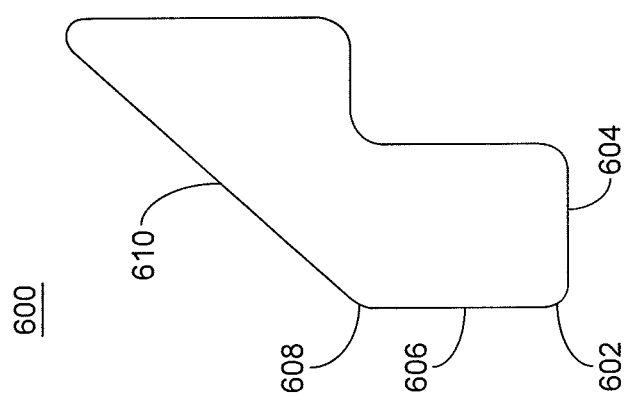

FIG. 6A shows a template 600 for providing a treatment profile. The template 600 can be substantially planar and include a first corner 602, from which a bottom edge 604 leads from. A side edge 606 extends vertically from the first corner 602 to a second corner 608. In some embodiments the side edge is approximately 10 mm long. A treatment guide feature 610 extends angularly from the second corner 608, which, in some embodiments, can be at an angle of 30 degrees with respect to the bottom edge 604. One or more ancillary edges complete the shape of the template 600 from the bottom edge to the treatment guide feature 610.

The template 600 can be constructed from thin flexible plastic sheet, and in some embodiments is transparent. In some embodiments the template includes an adhesive backing for temporarily adhering the template 600 to skin. In some embodiments the template 600 is constructed from an adhesive backed material, such as a bandage or tape. In some embodiments, the template may contain a transdermal medication, such as anti-inflammatory and anesthesia (e.g., lidocaine) drugs. An example of such construction is shown in U.S. Pub. No. 2010/0234471, which discloses lidocaine tape and is incorporated by reference herein.

In some embodiments the treatment guide feature 610 is a physical boundary of the template 600, as shown in FIG. 6A. However, in other embodiments, the treatment guide feature 610 may be placed within the template 600, such as a plurality of discreet openings (e.g., holes, slots), with each sized for one or more needle probes. In other embodiments, the treatment guide feature 610 is a printed feature on top of a needle penetrable material, such as tape or hydrogel. Although only one treatment guide feature 610 is shown, the template 600 may include a plurality of discrete treatment guide features for treating particular motor nerves.

In some embodiments, the template 600 can be electrically configured as a one-use "dongle" to enable function of a particular needle probe. For example, the template 600 can include a microchip that can physically or wirelessly (e.g., RFID) connect to a mutually coded needle probe, thus enabling the needle probe to function, in some embodiments for a limited time (e.g., 15 minutes), when a controller detects a match. Further, the controller can be configured to accept the code only once. In such embodiments, the template 600 cannot be effectively sterilized after use (e.g., adhesive backed). Thus, this configuration can help prevent the unethical reuse of treatment needle probes that are approved for only one-use.

FIG. 6B shows a an alternative embodiment of the template 600. In this embodiment, the template includes a heating element 612 for providing heat to skin during, and in some cases before, a treatment. The heating element 612 is placed adjacent to the treatment guide feature and coupled to an external or attached power source 612, such a switched battery. An example of applicable construction is shown in U.S. Pat. No. 4,518,851, which discloses a heated bandage and is incorporated by reference.

Figure 6C:
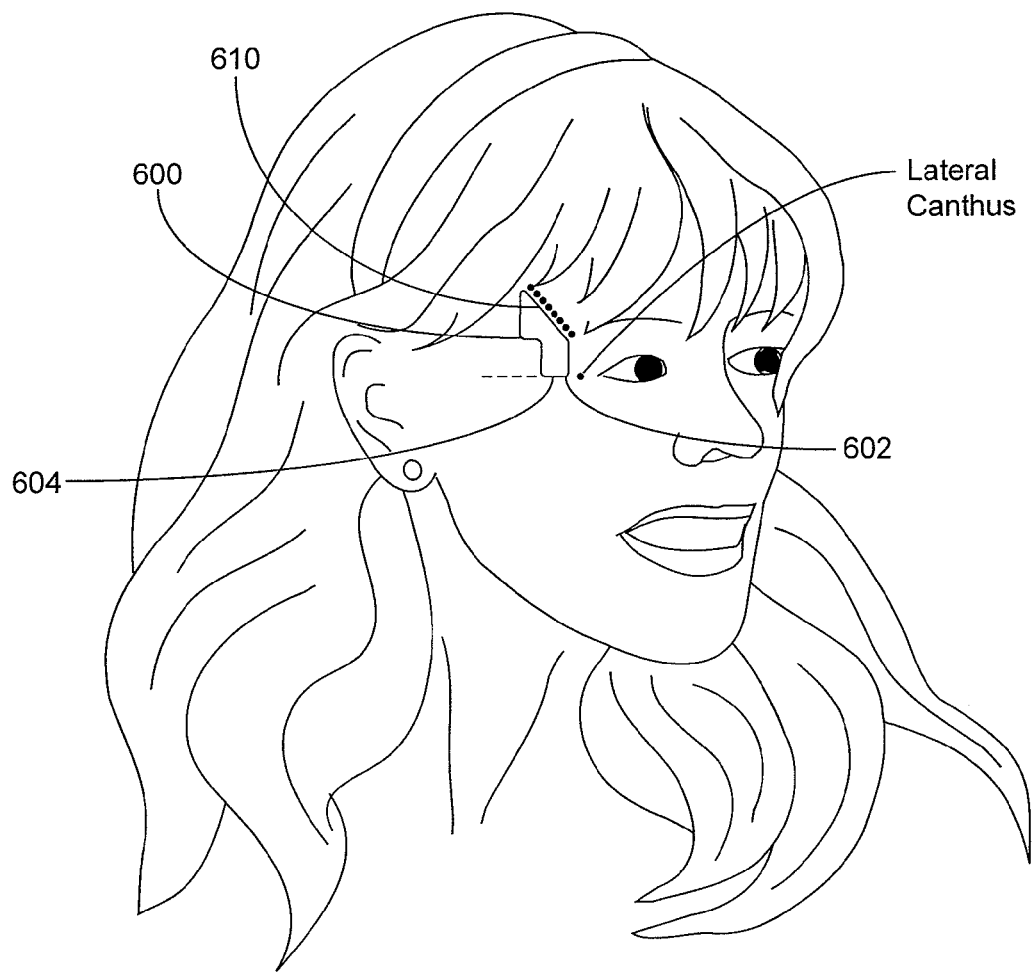
FIG. 6C is a perspective view of a portion of a method for using a treatment template, according to an embodiment of the invention.

FIG. 6C shows the template 600 in use in conjunction with the methods for treatment disclosed herein. The first corner 602 and bottom edge 604 an alignment feature for placing the template 600 on the temple region of the a face. As shown, the first corner 602 is placed adjacent to a lateral canthus on the temple region. The bottom edge 604 is made to be substantially horizontal with respect to the temple region when upright, i.e., along an anterior to posterior line. Proper placement of the alignment feature places the treatment guide feature 610 on a particular portion of the temple region, such that a treatment made along the treatment guide feature 610 will reliably treat particular motor nerves.

In some embodiments, the treatment path will effectively wall off a portion of the face for redundancy, e.g., with respect to the temple region a linear array of treatment can be performed from the lateral canthus region to the hair line. In other embodiments, only discrete portions of the treatment guide feature 610 are treated. Such portions can be marked on the treatment guide feature 610, or physically imparted (e.g., slots, holes, raised edges). The template 600 is not limited to using the lateral canthus as a facial alignment feature, for example, other facial features such as boney protrusions can be used as alignment features and the template 600 can be configured to place the treatment guide feature 610 accordingly.

Particular nerve location can vary with patients, and thus some treatment zones will be more efficacious than others for some patients. In some embodiments, the treatment guide feature 610 can include numerical markings or marked zones (e.g., lines, grid), which can also be marked with ink, and thus be used to record a "road-map" for future treatments on a particular patient. Accordingly, for following treatments, the prior road-map can be marked on a new template 600, or a customized template 600 can be made for that particular patient, and thus portions of the face which received prior efficacious treatment will be retreated and portions of the face where prior treatment had no effect will not be treated.

Depending on the particular configuration of the template 600, treatment may be performed along a particular edge, slot, or hole of the template 600. In other embodiments, the treatment guide feature 610 is used as a guide to draw an ink treatment line. In some embodiments, the template is adhered to the temple region of the face, for example, by exposing an adhesive backing of the template 600 and adhering the template to the temple region. In some embodiments, the template 600 may contain one or more medications, such as anti-inflammatory and anesthesia drugs (e.g., lidocaine) and accordingly may be placed prior to treatment (e.g., 15 minutes) to take effect. In some embodiments, heat may be applied prior and during treatment by activating one or more heating elements of the template 600 to raise the surface temperature of skin and/or to improve efficacy of transdermal medication.

While the exemplary embodiments have been described in some detail for clarity of understanding and by way of example, a number of modifications, changes, and adaptations may be implemented and/or will be obvious to those as skilled in the art. Hence, the scope of the present invention is limited solely by the claims as follows.

What is claimed is:

1. A method for cryogenically treating a target tissue to reduce or eliminate hyperdynamic wrinkles of a face of a patient, said method comprising:
   providing a cryogenic device having one or more tissue penetrating needle probes;
   advancing the one or more tissue penetrating needle probes through skin into the target tissue, the target tissue intersecting a motor nerve;
   providing a series of separate cooling treatments where the series of separate cooling treatments produce a treatment path along the target tissue to treat the motor nerve and to provide a continuous array of treated tissue in the face of the patient by:
   (1) cooling the target tissue with the one or more tissue penetrating needle probes at a first location;
   (2) retracting the one or more tissue penetrating needle probes after cooling the target tissue; and
   (3) positioning the one or more tissue penetrating needle probes such that cooling occurs at a subsequent location along the treatment path;
   (4) cooling the target tissue at the subsequent location such that the previously cooled target tissue and the subsequently cooled target tissue provide a continuous array of treated tissue in the face of the patient; and
   temporarily disrupting signal conduction from the motor nerve with the series of separate cooling treatments thereby preventing contraction of a muscle operably coupled to the motor nerve; and
   reducing or eliminating hyperdynamic wrinkles of a patient's face.

2. The method of claim 1, wherein the one or more tissue penetrating needle probe comprises a multi-needle array.

3. The method of claim 1, further comprising identifying anatomical landmarks prior to advancing the one or more tissue penetrating needle through the skin and drawing a treatment line on a surface of the skin based on a position of the identified anatomical landmarks so as to provide a visual path for the series of separate cooling treatments along the treatment path.

4. The method of claim 3, wherein the anatomical landmarks are identified by palpation, the anatomical landmarks at least including an outer edge of a lateral orbital rim or a temporal ridge of the patient.

5. The method of claim 3, wherein the anatomical landmarks are identified by applying electrical stimulation, imaging, or locally injecting a substance.

6. The method of claim 3, further comprising applying a treatment template to the patient's face by aligning one or more alignment features of the treatment template with one or more of the identified anatomical landmarks of the patient's face, the treatment template providing a treatment guide for identifying a linear array of cooling treatment locations spaced apart from the one or more anatomical landmarks for guiding the series of separate cooling treatments and for facilitating the drawing of the treatment line on the surface of the skin.

7. The method of claim 1, wherein the one or more tissue penetrating needle probes are inserted substantially perpendicular to the target tissue.

8. The method of claim 1, wherein the one or more tissue penetrating needle probes are inserted substantially parallel to a surface of the skin.

9. The method of claim 1, wherein the target tissue comprises the angular nerve, and wherein the one or more tissue penetrating needle probes are inserted adjacent the frontomaxillary suture or the frontonasal suture.

10. The method of claim 1, wherein the target tissue comprises the angular nerve, and wherein the one or more tissue penetrating needle probes are inserted inferior or medial to the infraorbital foramen.

11. A method for cryogenically treating a target tissue to reduce or eliminate hyperdynamic wrinkles of a patient's face, said method comprising:
providing a cryogenic device having one or more tissue penetrating needle probes;
advancing the one or more tissue penetrating needle probes through skin at a first location and into the target tissue adjacent a lateral edge of an orbital rim of the patient's face, the target tissue intersecting a motor nerve;
cooling the target tissue adjacent the lateral edge of the orbital rim of the patient's face with the one or more tissue penetrating needle probes;
after cooling the target tissue adjacent the lateral edge of the orbital rim of the patient's face, positioning the one or more tissue penetrating probes at a second location adjacent to the target tissue that is posterior from the lateral edge of the orbital rim and between the lateral edge of the orbital rim and a hairline of the patient;
cooling the target tissue at the second location with the one or more tissue penetrating needle probes such that the cooling treatment starts adjacent the lateral edge of an orbital rim on the patient's face and extends posteriorly toward the hairline of the patient's face; and
reducing or eliminating hyperdynamic wrinkles of a patient's face.

12. A method for cryogenically treating a target tissue to reduce or eliminate hyperdynamic wrinkles of a patient's face, said method comprising:
providing a cryogenic device having one or more tissue penetrating needle probes;
advancing the one or more tissue penetrating needle probes through skin at a first location and into the target tissue adjacent the tragus, the target tissue intersecting a motor nerve;
cooling the target tissue adjacent the tragus with the one or more tissue penetrating needle probes;
after cooling the target tissue adjacent the tragus, positioning the one or more tissue penetrating probes at a second location adjacent to the target tissue that is anterior to the first location along a zygomatic arch;
cooling the target tissue at the second location with the one or more tissue penetrating needle probes such that the cooling treatment starts adjacent the tragus and progresses anteriorly along the zygomatic arch of the patient's face; and
reducing or eliminating hyperdynamic wrinkles of a patient's face.

13. The method of claim 1, wherein the disruption comprises Wallerian degeneration of the motor nerve.

14. The method of claim 1, wherein a temporal branch of the motor nerve adjacent an orbital rim is temporarily disrupted.

15. The method of claim 1, further comprising protecting the skin disposed above the target tissue from cooling induced injury.

16. The method of claim 15, wherein protecting comprises heating the skin disposed above the target tissue.

17. The method of claim 1, further comprising locally anesthetizing a portion of a patient's face.

18. A method for cryogenically treating a target tissue, said method comprising:
providing a cryogenic device having one or more tissue penetrating needle probes;
providing a treatment template having an alignment feature corresponding to an anatomical landmark on a face of a patient and a treatment guide configured to indicate a treatment path spaced apart from the anatomical landmark on the face of the patient that is associated with the alignment feature;
aligning the treatment template on a temple region of the face of the patient by aligning the alignment feature of the treatment template with the corresponding anatomical landmark on the face of the patient;
maintaining the treatment template on the temple region and drawing the treatment path on a surface of the skin as indicated by the treatment guide;
advancing along the drawn treatment path the one or more tissue penetrating needle probes into the target tissue, the target tissue intersecting a motor nerve;
cooling the target tissue along the treatment path with the one or more tissue penetrating needle probes so as to provide a continuous array of treated tissue in the face of the patient;
temporarily disrupting signal conduction from the motor nerve thereby preventing contraction of a muscle operably coupled to the motor nerve; and
reducing or eliminating hyperdynamic wrinkles of a patient's face.

19. The method of claim of claim 18, wherein the alignment feature comprises a first corner of the treatment template, wherein a bottom edge of the treatment template leads from the first corner of the treatment template, and wherein a side edge of the treatment template leads from the first corner of the treatment template to a second corner of the treatment template in a direction perpendicular to the bottom edge.

20. The method of claim 19, wherein the anatomical landmark corresponding to the alignment feature comprises a lateral canthus of the temple region, and wherein aligning the treatment template comprises placing the first corner of the treatment template at the lateral canthus on the temple region.

21. The method of claim 20, wherein aligning the treatment template further comprises aligning the bottom edge in an anterior to posterior direction such that the bottom edge extends in the posterior direction from the first corner of the treatment template.

22. The method of claim 20, wherein the treatment guide extends from the second corner at an angle of approximately 30 degrees with respect to the bottom edge of the treatment template so as to identify a linear array of treatment locations from the lateral canthus region to the hairline of the user when aligned on the temple region of the face of the patient.

23. The method of claim of claim 18, wherein the treatment template comprises a flexible transparent plastic sheet.

24. The method of claim of claim 18, wherein the treatment template comprises an adhesive tape.

25. The method of claim of claim 24, wherein the adhesive tape includes a medication.

26. The method of claim of claim 24, wherein the treatment template includes a heating element configured to heat a region of skin along the treatment guide of the treatment template.

27. The method of claim 26, further comprising heating the skin during cooling using the heating element of the treatment template.

28. A template for cryogenically treating a target tissue, the template comprising:
 a planar body having an alignment feature for aligning the planar body with a lateral canthus on a temple region of a face, the temple region having target tissue;
 a treatment guide being configured to identify a linear array of treatment locations relative to the lateral canthus on the temple region of the to provide a continuous array of treated tissue in the face of the patient with the cryogenic treatment, the identified linear array of treatment locations providing a guide for one or more tissue penetrating needle probes to advance through skin into the target tissue, the target tissue intersecting a motor nerve.

29. The template of claim 28, wherein the alignment feature comprises a first corner, wherein a bottom edge leads from the first corner, and wherein a side edge leads from the first corner to a second corner in a direction perpendicular to the bottom edge.

30. The template of claim 29, wherein the treatment guide extends from the second corner at an angle of approximately 30 degrees with respect to the bottom edge of the treatment template so as to identify the linear array of treatment locations from the lateral canthus region to the hairline of the user when aligned on the temple region of the face of the patient.

31. The template of claim of claim 28, wherein the planar body comprises a flexible transparent plastic sheet.

32. The template of claim of claim 28, wherein the planar body comprises adhesive tape.

33. The template of claim of claim 32, wherein the adhesive tape includes a medication.

34. The template of claim of claim 32, further comprising a heating element configured to heat a region along the treatment guide.

35. The method of claim 1, wherein providing the series of separate cooling treatments further comprises: (5) checking an effect of the cooling treatment; and (6) repeating steps (2)-(5) until a desired effect is achieved.

36. The method of claim 1, wherein providing the series of separate cooling treatments further comprises: (5) repeating steps (2)-(4) until the series of separate cooling treatments reaches a hairline of the patient.

37. The method of claim 1, wherein the series of separate cooling treatments progresses in an anterior to posterior direction along the target tissue.

38. The method of claim 37, wherein the series of separate cooling treatments progresses in the anterior to posterior direction toward a hairline of the patient.

39. The method of claim 1, wherein the series of separate cooling treatments progresses in a posterior to anterior direction along the target tissue.

40. The method of claim 6, further comprising activating a heating element of the treatment template to heat the skin of the patient adjacent the linear array of cooling treatment locations, and wherein the heating element is coupled with a battery, and wherein activating the heating element of the treatment template comprises delivering power from the battery to the heating element.

41. The method of claim 27, wherein the heating element of the treatment template is coupled with a battery, and wherein heating the skin during cooling using the heating element of the treatment template comprises delivering power from the battery to the heating element.

42. The template of claim 34, wherein the heating element is coupled with a battery.

* * * * *